US008287890B2

(12) United States Patent
Elton

(10) Patent No.: US 8,287,890 B2
(45) Date of Patent: Oct. 16, 2012

(54) HYDROPHILIC COATING

(75) Inventor: Richard K. Elton, Queensbury, NY (US)

(73) Assignee: C.R. Bard, Inc., Murray Hill, NJ (US)

( * ) Notice: Subject to any disclaimer, the term of this patent is extended or adjusted under 35 U.S.C. 154(b) by 402 days.

(21) Appl. No.: 12/638,464

(22) Filed: Dec. 15, 2009

(65) Prior Publication Data
US 2011/0144579 A1   Jun. 16, 2011

(51) Int. Cl.
A61K 9/00 (2006.01)

(52) U.S. Cl. ........ 424/400; 424/422; 424/423; 424/424; 424/426; 424/78.17

(58) Field of Classification Search .......................... None
See application file for complete search history.

(56) References Cited

U.S. PATENT DOCUMENTS

| 4,100,309 A | 7/1978 | Micklus et al. |
| 4,119,094 A | 10/1978 | Micklus et al. |
| 4,154,244 A | 5/1979 | Becker et al. |
| 4,481,323 A | 11/1984 | Sterling |
| 4,585,666 A | 4/1986 | Lambert |
| 4,906,237 A | 3/1990 | Johansson et al. |
| 4,973,493 A | 11/1990 | Guire |
| 4,979,959 A | 12/1990 | Guire |
| 5,002,582 A | 3/1991 | Guire et al. |
| 5,077,352 A | 12/1991 | Elton |
| 5,160,559 A | 11/1992 | Scovil et al. |
| 5,160,790 A | 11/1992 | Elton |
| 5,179,174 A | 1/1993 | Elton |
| 5,263,992 A | 11/1993 | Guire |
| 5,290,585 A | 3/1994 | Elton |
| 5,295,978 A | 3/1994 | Fan et al. |
| 5,385,152 A | 1/1995 | Abele et al. |
| 5,414,075 A | 5/1995 | Swan et al. |
| 5,507,804 A | 4/1996 | Llanos |
| 5,509,899 A | 4/1996 | Fan et al. |
| 5,512,329 A | 4/1996 | Guire et al. |
| 5,558,900 A | 9/1996 | Fan et al. |
| 5,576,072 A | 11/1996 | Hostettler et al. |
| 5,620,738 A | 4/1997 | Fan et al. |
| 5,637,460 A | 6/1997 | Swan et al. |
| 5,645,931 A | 7/1997 | Fan et al. |
| 5,662,960 A | 9/1997 | Hostettler et al. |
| 5,693,034 A | 12/1997 | Buscemi et al. |
| 5,702,754 A | 12/1997 | Zhong |
| 5,756,144 A | 5/1998 | Wolff et al. |
| 5,789,018 A | 8/1998 | Engelson et al. |
| 5,800,412 A | 9/1998 | Zhang et al. |
| 5,908,656 A | 6/1999 | Ishikawa et al. |
| 5,919,570 A | 7/1999 | Hostettler et al. |
| 6,017,577 A | 1/2000 | Hostettler et al. |
| 6,030,656 A | 2/2000 | Hostettler et al. |
| 6,071,266 A | 6/2000 | Kelley |
| 6,077,698 A | 6/2000 | Swan et al. |
| 6,080,488 A | 6/2000 | Hostettler et al. |
| 6,120,904 A | 9/2000 | Hostettler et al. |
| 6,176,849 B1 | 1/2001 | Yang et al. |
| 6,221,425 B1 | 4/2001 | Michal et al. |
| 6,238,799 B1 | 5/2001 | Opolski |
| 6,254,634 B1 | 7/2001 | Anderson et al. |
| 6,265,016 B1 | 7/2001 | Hostettler et al. |
| 6,270,902 B1 | 8/2001 | Tedeschi et al. |
| 6,278,018 B1 | 8/2001 | Swan |
| 6,287,285 B1 | 9/2001 | Michal et al. |
| 6,306,454 B1 | 10/2001 | Ung-Chhun et al. |
| 6,368,658 B1 | 4/2002 | Schwarz et al. |
| 6,444,324 B1 | 9/2002 | Yang et al. |
| 6,458,867 B1 | 10/2002 | Wang et al. |
| 6,558,798 B2 | 5/2003 | Zhong et al. |
| 6,589,215 B2 | 7/2003 | Yang et al. |
| 6,603,040 B1 | 8/2003 | Swan |
| 6,610,035 B2 | 8/2003 | Yang et al. |
| 6,629,961 B1 | 10/2003 | Israelsson et al. |
| 6,656,517 B2 | 12/2003 | Michal et al. |
| 6,673,053 B2 | 1/2004 | Wang et al. |
| 6,706,025 B2 | 3/2004 | Engelson et al. |
| 6,706,408 B2 | 3/2004 | Jelle |
| 6,709,706 B2 | 3/2004 | Zhong et al. |
| 6,866,936 B2 | 3/2005 | Opolski |
| 7,008,979 B2 | 3/2006 | Schottman et al. |
| 7,025,752 B2 | 4/2006 | Rice et al. |
| 7,112,298 B2 | 9/2006 | Kampa et al. |
| 7,141,246 B2 | 11/2006 | McGhee |
| 7,220,491 B2 | 5/2007 | Rouns et al. |
| 7,402,620 B2 | 7/2008 | McGhee |
| 7,431,714 B2 | 10/2008 | Rice et al. |
| 7,476,214 B2 | 1/2009 | Sydney et al. |
| 7,544,381 B2 | 6/2009 | Kangas |

FOREIGN PATENT DOCUMENTS

WO    WO 00/27897    5/2000

Primary Examiner — James Rogers
(74) Attorney, Agent, or Firm — King & Schickli, PLLC

(57) ABSTRACT

A hydrophilic, lubricious coating for a substrate includes a first coating layer having a cross-linked polyurethane or polyurea complexed with poly(ethylene oxide) formed by reacting a mixture of an isocyanate, a polyol or polyamine, and a poly(ethylene oxide), and a second coating layer having a cross-linked polyurethane or polyurea complexed with polyvinylpyrrolidone formed by reacting a mixture of an isocyanate, a polyol or polyamine, and a polyvinylpyrrolidone. The first layer is substantially covered by the second layer and the second layer at least partially interpenetrates the first layer. The coating is provided by applying the first coating layer, curing to provide a cross-linked polyurethane or polyurea/poly(ethylene oxide) coating, applying the second layer, and curing to provide a cross-linked polyurethane or polyurea/polyvinylpyrrolidone coating.

19 Claims, 2 Drawing Sheets

HYDROPHILIC COATING

FIELD OF THE INVENTION

Generally, the present invention relates to hydrophilic, lubricious coatings for substrates. Particularly, it relates to hydrophilic, lubricious coating compositions including a first, lubricious base layer and a second, lubricious top layer. Methods for applying such hydrophilic, lubricious coatings, and medical devices so coated, are provided. Exemplary devices which may be coated with the hydrophilic, lubricious coatings of the present invention include catheters, balloon catheters, and the like.

BACKGROUND OF THE INVENTION

It is known in the art to provide hydrophilic coatings with low friction (coefficient of friction of 0.3 or less) for medical devices such as catheters, balloon catheters, catheter introducers, and the like. When such low friction surfaces are used, devices having such surfaces slide easily within passageways such as arteries, veins, cannulae and other body orifices. A variety of methods are known for providing desirable low friction surfaces for medical devices.

For example, an outer portion of the medical device may be fabricated of a material having desirable low-friction properties such as TEFLON or other such materials. Unfortunately, combining particular low-friction materials with other desired properties for the medical device, such as flexibility, is often not possible.

For that reason, hydrophilic, lubricious coatings are known for medical devices to provide the desired anti-friction properties. One such coating may be formed from combinations of isocyanate, polyurethane, and polyvinylpyrrolidone (PVP). Other such coatings have been provided with combination of isocyanate and/or polyurethane in with polyethylene oxide) (PEO). Still further, combinations of isocyanate, polyols or polyamines, and PVP or PEO are known to provide the desired low-friction properties for medical device surfaces. As examples, such PVP and PEO-based coatings are disclosed in U.S. Pat. Nos. 5,160,790 and 5,179,174 to Elton.

While effective for their intended purpose, improvements in such coatings are possible. For example, polyvinylpyrrolidone-based coatings, while suitably flexible and lubricious, may abrade during use, exposing portions of the coated medical device and reducing the overall anti-friction properties of the coated device. Poly(ethylene oxide)-based coatings, while providing superior abrasion resistance, are not as soft and generally not as lubricious as polyvinylpyrrolidone-based coatings.

The present disclosure addresses a need in the art by providing hydrophilic, lubricious coatings for medical devices which, while providing the desired anti-friction properties, retain those anti-friction properties even in the event a portion of the coatings abrade during use. In particular, hydrophilic, lubricious coatings including a first layer comprising PEO and a second layer comprising PVP are disclosed. In the event the second, PVP-based layer abrades, the coated device retains its anti-friction properties due to the more durable, PEO-based first layer.

SUMMARY OF THE INVENTION

The above-mentioned and other problems become solved by applying the principles and teachings associated with the hereinafter-described methods for providing hydrophilic, lubricious coatings to an exterior surface of a medical device such as a catheter, a balloon catheter, or other such device, and compositions of such coatings. Broadly, the present disclosure provides hydrophilic, lubricious coating compositions comprising a first, poly(ethylene oxide)-based layer and a second, polyvinylpyrrolidone-based layer. Still further, methods for applying such coatings are described.

Generally, in one aspect of the invention there is described a hydrophilic, lubricious coating for a substrate, which includes a first, abrasion-resistant layer having a cross-linked polyurethane/poly(ethylene oxide) component formed by reacting a mixture of an isocyanate, a polyol or polyamine, and a poly(ethylene oxide). The lubricious coating further includes a second layer having a cross-linked polyurethane/polyvinylpyrrolidone component formed by reacting a mixture of an isocyanate, a polyol or polyamine, and a polyvinylpyrrolidone. The first layer may be substantially covered by the second layer, and the second layer may at least partially interpenetrate the first layer.

In another aspect, there is provided a method for providing a hydrophilic, lubricious coating on an exterior surface of a substrate. The method includes the steps of applying a first, abrasion-resistant layer comprising a mixture of an isocyanate, a polyol, and a poly(ethylene oxide) and curing the first, abrasion-resistant layer to provide a cross-linked polyurethane/poly(ethylene oxide) coating. Next is the step of applying a second layer comprising a mixture of an isocyanate, a polyol, and a polyvinylpyrrolidone and curing the second layer to provide a cross-linked polyurethane/polyvinylpyrrolidone coating. By the described method is provided a two-layer, lubricious coating wherein the first layer is substantially covered by the second layer and the second layer at least partially interpenetrates the first layer.

Application of the first and second layers according to the present disclosure may be by any one of dipping, spraying, brushing, rolling, or wiping. The recited curing steps may be accomplished by baking the coated substrate at temperature. Suitable substrates for coating according to the present methods include medical devices such as catheters, balloon catheters, urinary catheters, catheter introducers, medical wires, stents, stent grafts, dilation balloons, and the like.

These and other embodiments, aspects, advantages, and features of the present invention will be set forth in the description which follows, and in part will become apparent to those of ordinary skill in the art by reference to the following description of the invention and referenced drawings or by practice of the invention. The aspects, advantages, and features of the invention are realized and attained by means of the instrumentalities, procedures, and combinations particularly pointed out in the appended claims.

BRIEF DESCRIPTION OF THE DRAWING

The accompanying drawing incorporated in and forming a part of the specification, illustrates several aspects of the present invention, and together with the description serves to explain the principles of the invention. In the drawing.

DETAILED DESCRIPTION OF THE ILLUSTRATED EMBODIMENTS

Figure 1:
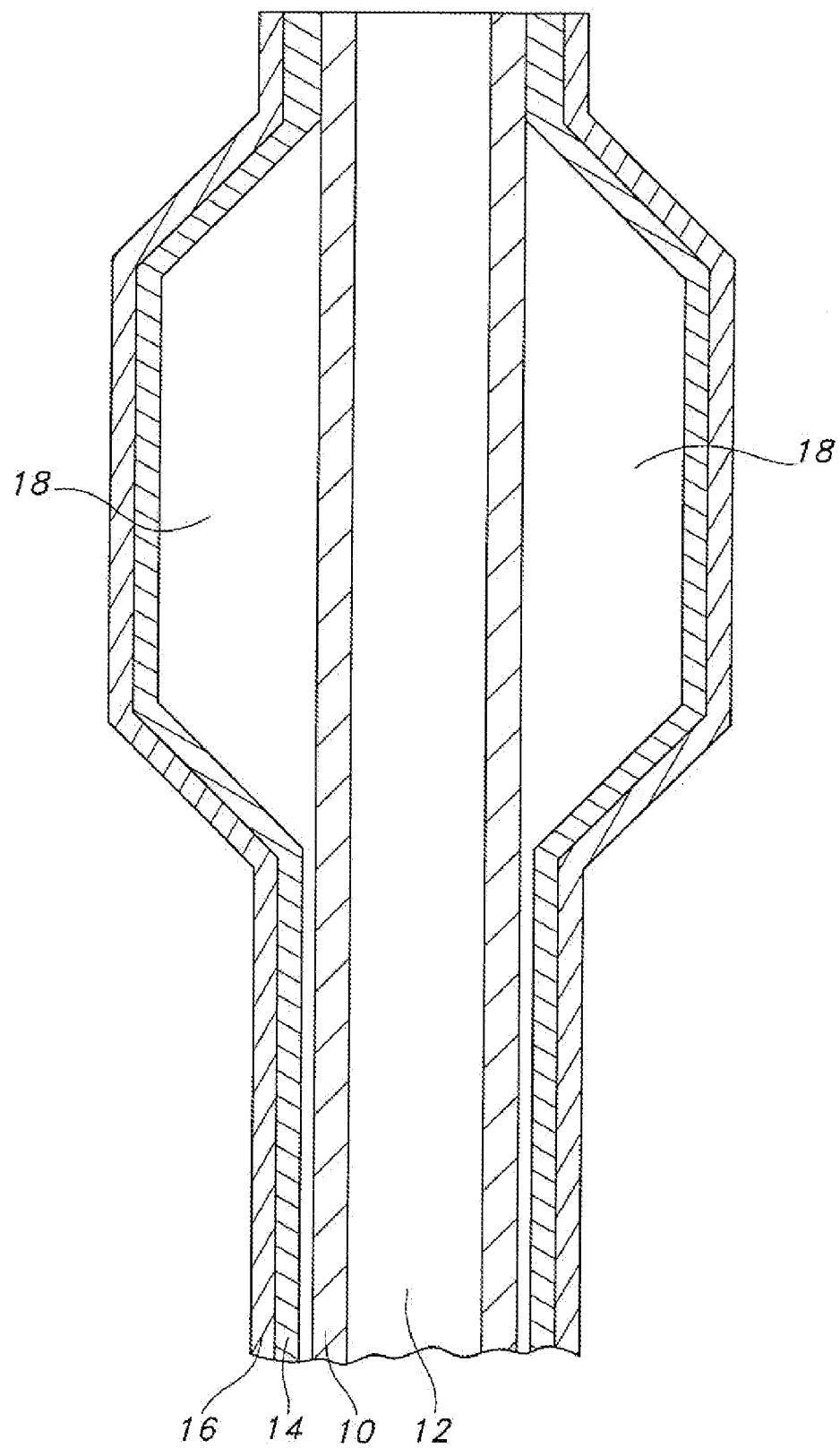
FIG. 1 is a cross-sectional view of a portion of a balloon catheter, including a shaft and balloon coated with a flexible, hydrophilic and lubricious coating according to the invention.

In the following detailed description of the illustrated embodiments, reference is made to the accompanying drawings that form a part hereof, and in which is shown by way of illustration, specific embodiments in which the invention may be practiced. These embodiments are described in sufficient detail to enable those skilled in the art to practice the invention and like numerals represent like details in the various figures. Also, it is to be understood that other embodiments may be utilized and that process, mechanical, arrangement, and/or other changes may be made without departing from the scope of the present invention.

In accordance with the present disclosure, hydrophilic, lubricious coatings for medical devices, and devices so coated, are provided. The coatings include two hydrophilic, lubricious layers. Broadly, the first lubricious layer is disposed adjacent the medical device surface, and includes at least an isocyanate/polyol component or an isocyanate/polyamine component, and a polyethylene oxide) component. The second layer, which may substantially overlay the first layer, includes at least an isocyanate/polyol component or an isocyanate/polyamine component, and a polyvinylpyrrolidone component. The coatings may be applied to a variety of medical devices formed of known substrates by conventional coating application methods.

Devices which may be coated with the coatings described herein include without limitation catheters, balloon catheters (including the balloon catheter shaft, balloon, or both), introducers, body implants, medical wires, stents, stent grafts, tubing, dilation balloons, and the like. Such devices may be fabricated of any suitable material as is known in the art for such purposes. Typically, substrate materials will be selected which provide functional groups, including carboxylic acids, —OH groups, —NH groups, —SH groups, or the like, which react suitably with the isocyanate component of the present coatings.

The present coatings may also be applied to devices providing a metal surface. Typically a primer layer will be applied to such metal substrates prior to application of the present coatings, to enhance bonding of the first lubricious layer with the metal substrate. Such primers are disclosed in U.S. Pat. No. 6,270,902, and may include a number of compositions for providing the desired functional groups for reaction with the isocyanate component of the first coating layer. Examples include without limitation ethyl vinyl alcohol, isocyanate-terminated prepolymers, polyurethane, epoxies, and NCO and OH-functional silanes.

Examples of organic substrates that can be coated with the coatings of this invention include plastics and other polymers, such as nylon, polyether block amide, polyethylene terephthalate, polyetherurethane, polyesterurethane, other polyurethanes, natural rubber, rubber latex, synthetic rubbers, polyester-polyether copolymers, polycarbonates, and other organic materials. Some of these materials are available under the trademarks such as PEBAX available from Arkema, Inc. of Philadelphia, Pa., MYLAR available from E. I. duPont deNemours and Co. of Wilmington, Del., TEXIN from Mobay Corporation of Pittsburgh, Pa., PELLETHANE available from Dow Chemical of Midland, Mich., ESTANE from Lubrizol Corporation of Brecksville Ohio, and LEXAN available from SABIC of Pittsfield, Mass.

In an embodiment of the invention, a highly lubricious coating is formed overlying a substrate, in the depicted embodiments (see FIGS. 1 and 2) being a balloon catheter including a shaft 10 defining a hollow lumen 12 and a balloon 18 concentrically arranged about a distal end of the shaft 10. The coating is formed of two hydrophilic, lubricious coating layers 14, 16 formed of flexible organic polymeric materials. The coatings may be applied by a variety of methods, including dipping, spraying, wiping, painting, rolling, brushing, and the like. For convenience, the coatings will typically be applied by dipping a medical device in a solution containing the desired coating material.

For the first coating layer 14, the coating comprises at least a mixture of isocyanate, a polyol or polyamine, and a poly (ethylene oxide). A ratio of weight of polyurethane or polyurea solids (from the combination of isocyanate and polyol or polyamine): poly(ethylene oxide) may be selected to be from about 0.25 to about 6.0. The weight ratio will typically be from about 0.7 to about 5.0 according to the particular isocyanate and polyol or polyamine selected for the first coating layer 14.

The stoichiometric ratio of total NCO groups in the isocyanate to total —OH groups in the polyol (or —NH groups, if a polyamine is used) for the first coating layer 14 can vary from about 0.6 to about 3.5. Generally, in producing a polyurethane or polyurea of controllable composition from an isocyanate/polyol or polyamine mixture, it is preferable to use an NCO to —OH or —NH ratio close to 1.0. Typically, a ratio of from about 1.05 to about 1.3 NCO:OH will be selected to provide a slight excess of isocyanate, providing for suitable bonding of the first coating layer 14 to the substrate via interactions between the free isocyanate groups of the coating layer 14 mixture and the functional groups present in the underlying substrate. Of course, the particular NCO:OH ratio selected will vary in accordance with the substrate of choice, the properties of the specific polyols or polyamines used, and the desired properties of the final coating. For the first coating layer 14 mixture, an NCO:OH ratio of 1.1:1 is typically selected.

Isocyanates having at least two unreacted isocyanate groups per molecule are suitable, including without limitation polymethylenepolyphenyl isocyanate, 4,4'-diphenylmethane diisocyanate and position isomers thereof, 2,4-toluene diisocyanate and position isomers thereof, 3,4-dichlorophenyl diisocyanate and isophorone isocyanate, adducts or prepolymers of isocyanates and polyols such as the adduct of trimethylolpropane and diphenylmethane diisocyanate or toluene diisocyanate. Further examples of polyisocyanates useful in this invention may be found in the ICI Polyurethanes Book, George Woods, published by John Wiley and Sons, New York, N.Y. (1987) and the Encyclopedia of Polymer Science and Technology, H. F. Mark, N. G. Gaylord and N. M. Bikales (eds.), (1969), the disclosures of each of which are incorporated herein in their entirety by reference. A preferred isocyanate for use in the present invention provides about 11.9% NCO, available in one embodiment from Bayer as Desmodur L 67 MPA/X.

Suitable polyols may be any of a large number of polyols reactive with the isocyanates to form polyurethanes as is known in the art. Examples of suitable polyols include without limitation polyester polyols, polyether polyols, modified polyether polyols, polyester ether polyols, castor oil polyols and polyacrylate polyols. Specific polyols further include castor oil and castor oil derivatives (triglyceride of 12-hydroxyoleic acid), poly(ethylene adipates), poly(diethyleneglycol adipates, polycaprolactone diols and polycaprolactonepolyadipate copolymer dials, poly (ethyleneterephthalate) polyols, polycarbonate diols, N,N,N'N'-tetrakis(α hydroxypropyl)ethylenediamine, polytetramethylene ether glycol, ethyleneoxide adducts of polyisopropylene diols, ethylene oxide adducts of polyisopropylene triols. Particular example polyols include DESMOPHEN 1800, DESMOPHEN A365, DESMOPHEN 651A-65, DESMOPHEN 1300 75, DESMOPHEN 800, DESMOPHEN A160, DESMOPHEN 550 DU, DESMOPHEN 1600U, DESMOPHEN 1920D, and DESMOPHEN 1150 all available from Bayer Corporation of Pittsburgh, Pa. Other suitable polyols include castor oil (triglyceride of 12-hydroxy oleic acid) and castor oil derivatives, such as DB oil, POLYCIN 12, POLYCIN 53 and POLYCIN 99F all available from Vertellus, Inc. of Bayonne, N.J. Suitable dials include poly(ethylene adipates), poly(diethyleneglycol adipates), polycaprolactone diols and polycaprolactone-polyadipate copolymer diols, poly(ethyleneterephthalate) polyols, polycarbonate diols, polytetramethylene ether glycol, ethylene oxide adducts of polyoxypropylene diols, ethylene oxide adducts of polyoxypropylene triols. Many other suitable polyols are available as known to those skilled in this art.

Suitable polyamine products may be selected from any of a large number of polyamines reactive with isocyanate to form polyureas as is known in the art. Non-limiting examples of suitable polyamine products include Jeffamine D-230, Jeffamine D-400, Jeffamine D-2000, Jeffamine T-403, Jeffamine T-5000, and Jeffamine T-3000 available from Huntsman Corporation of The Woodlands, Tex. Melamine and melamine derivatives may also be used, available from many chemical supply companies. Heterocyclic diamines and amine adducts may also be used. Additional suitable polyamines are available as known to those skilled in the art.

The solvents selected for the invention used are preferably those that do not react with the isocyanate, the polyol or the poly(ethylene oxide) but are solvents for all. The solvents preferably are free of reactive amine, hydroxyl and carboxyl groups. The solvent should further preferably be capable of dissolving the isocyanate, polyol, and poly(ethylene oxide). Suitable solvents include but are not limited to methylene bromide, methylene chloride, chloroform, dichloroethane, acetonitrile, methyl benxoate, benzyl acetate, n-propyl bromide, cyclohexanone, dichloethylene, 1,3-dioxolane and N-methyl pyrrolidone. Other solvents meeting the above objectives are also suitable.

A solids contents for the first coating layer 14 mixture in a range of from about 0.4 to about 40% is contemplated, but will vary according to the solvent selected, the desired thickness of the coating, the viscosity properties of the particular grade of poly(ethylene oxide) selected, and other factors. When methylene chloride is used as solvent, the solids content of the coating solution may be 1 to 15% (w/w) and preferably 2.25 to 4% (w/w). When dibrornomethane is used, the solids content of the coating solution may be 0.4 to 10% (w/w) and preferably 1.2 to 2.5% (w/w). Thus, the solids content of the first coating layer 14 solution will vary according to a number of factors.

The poly(ethylene oxide) selected will typically be from the group having an average molecular weight of from about 80,000 to about 5,000,000. Typically, a poly(ethylene oxide) will be selected from the group having an average molecular weight of from about 200,000 to about 600,000, since use of poly(ethylene oxide)s having an average molecular weight in excess of 600,000 may create problems with viscosity of the resultant mixture. Commercially available poly(ethylene oxide) products include ALKOX R-150, ALKOX R-400, ALKOX E-45, ALKOX E-75, ALKOX E-240 all from Meisei Chemical Works, Ltd of Kyoto, Japan, and P-20 Grade Poly(ethylene oxide) available from Ring Specialty Chemicals, of Toronto, Ontario, Canada.

For convenience of application, the first coating layer 14 mixture may be provided as a solution. The first coating layer 14 mixture in solution form is prepared by weighing the appropriate quantities of isocyanate, polyol or polyamine, poly(ethylene oxide), and solvent stock solutions into an appropriate mixing vessel. Additional solvents may be added to adjust the viscosity as needed. This solution is mixed well and may then be applied to an appropriate medical device, such as by dipping, spraying, wiping, painting, rolling, and the like.

Typically, a medical device such as a catheter, balloon catheter, and the like will be dipped into the coating layer 14 mixture by dipping for a period sufficient to wet the device. A dipping time of from a few seconds to a few minutes typically suffices, although longer time periods are contemplated according to the device being coated and the material of which the device is fabricated.

After applying the first coating solution, the solvent may be allowed to evaporate from the coated substrate 10 such as by exposure to ambient conditions for from 10 to 180 minutes, but can be evaporated at temperatures of from 35° F. to 400° F. for time periods of a few seconds to overnight, depending upon the selection of solvent and the speed with which evaporation is desired. In the case of a medical device such as a catheter, balloon catheter, etc., the device may be hung from a proximal end thereof whereby the liquid coating solution is drawn by gravity towards the distal tip of the device. The time frame for evaporation will typically be kept short to allow suitable solvent evaporation without significant reaction of atmospheric moisture with the isocyanate component of the first coating layer 14 mixture.

The first coating layer 14 is then cured. Suitable cure times/temperatures will vary with the choice of isocyanate and polyol and the composition of the substrate. A device such as a balloon catheter having a balloon which is typically more temperature sensitive, than, for example, the catheter shaft, will typically be cured at lower temperatures for a longer time period. In a typical embodiment, the first coating layer 14 may be cured by oven baking at about 165° F. for about 4 hours. For a less temperature sensitive substrate, baking at higher temperatures such as about 250° F. for a few minutes may suffice.

Next, a second coating layer 16 is formed from a mixture containing an isocyanate, a polyol or polyamine, and polyvinylpyrrolidone. For convenience of application, the second coating layer 16 mixture is typically provided as a solution, such as in a carrier liquid. The ratio of weight of the polyurethane formed in situ to the polyvinylpyrrolidone may vary from 0.05 to 3.0 and is preferably from 0.30 to 1.0. In order to provide a hydrogel having the desired lubriciousness, the ratio of polyurethane: polyvinylpyrrolidone will typically be kept at 1.0 or less.

The stoichiometric ratio of total NCO groups in the isocyanate to total OH groups in the polyol (or to total —NH groups in the polyamine) can vary from 0.75 to 3.0. As noted above, generally in producing a polyurethane of controllable composition, it is preferable to use an NCO to —H or —NH ratio close to 1.0. However, as before, typically the ratio is adjusted to somewhat greater than 1.0 since it is known that isocyanates readily react with water, and that incidental quantities of water can integrate with the uncured coating. This water is present from various sources such as atmospheric moisture, moisture in solvent, or moisture associated with the polyvinylpyrrolidone. A typical NCO:OH ratio for the second coating layer 16 mixture will be 1.3:1.

Polyvinylpyrrolidones suitable for use in the present coatings have an average molecular weight of from about 50,000 to 2.5 million. Examples of suitable polyvinylpyrrolidone materials include those available from BASF Corp, Parsippany, N.J. as KOLLIDON 90 F, and KOLLIDON 30, and those available from GAF Corporation, as PLASDONE K-90, PLASDONE K-30, and PLASDONE K-25.

Commercially available polyvinylpyrrolidone products typically contain approximately 3-5% (w/w) water. Further-more, polyvinylpyrrolidone is very hygroscopic, and tends to accumulate water on normal storage when exposed to air. Since water is very reactive toward isocyanates, it is desirable, but not essential, to reduce the water content to less than 0.5% prior to use in preparing coating formulations. This may be readily accomplished by drying an appropriate quantity of polyvinylpyrrolidone, for example, by heating it for several hours at 220° F.

The isocyanate used will typically be selected from the group of isocyanates as described above, that is, isocyanates having at least two unreacted isocyanate groups per molecule. Polyols useful in this invention can be any of a large number of polyols reactive with the isocyanates to form polyurethanes as described above. Typically, a different polyol or polyols will be selected for the second coating layer 16 mixture, although it is contemplated to use the same polyol or polyols as for the first coating layer 14 mixture.

Suitable solvents will not react with the isocyanate, the polyol or the polyvinylpyrrolidone, but are solvents for all. The solvents must be free of reactive groups such as, for example, amine, hydroxyl and carboxyl groups. The solvent must further be capable of dissolving the isocyanate, polyol, and polyvinylpyrrolidone. The coating solution should also be substantially free of water which may react with the isocyanate groups. Thus, it is preferred that the solvent be very dry, that is, that the water content of the solvent used be very low, (e.g., less than 100 ppm). Suitable solvents available commercially in a suitably dry form include but are not limited to methylene bromide, methylene chloride, chloroform, dichloroethane, acetonitrile, n-propyl bromide, 1,3-dioxolane, N-methylpyrrolidone and dichloroethylene. When methylene chloride is used, the solids content of the coating solution may be 1 to 15% (w/w) and preferably 2.25 to 4% (w/w). When dibromomethane is used, the solids content of the coating solution may be 0.4 to 10% (w/w) and preferably 1.2 to 2.5% (w/w). As with the PEO coatings described earlier, the solids content of the second coating layer 16 solution will vary according to the solvent of choice, the desired thickness of the coating, the viscosity properties of the particular grade of polyvinylpyrrolidone selected, and other factors. Other solvents meeting the above objectives are also suitable.

The second coating layer 16 mixture may be prepared by weighing the appropriate quantities of isocyanate, polyol or polyamine, polyvinylpyrrolidone, and solvent stock solution and adding them into an appropriate mix vessel. Additional solvents can be added to adjust the viscosity and solids content. Solids contents may be in a range of from 0.4 to 15% (w/w), with 1.5 to 4% (w/w) preferred, depending on the solvent used and other considerations. This solution is mixed well and then applied to a desired substrate such as a catheter or a balloon catheter.

Figure 2:
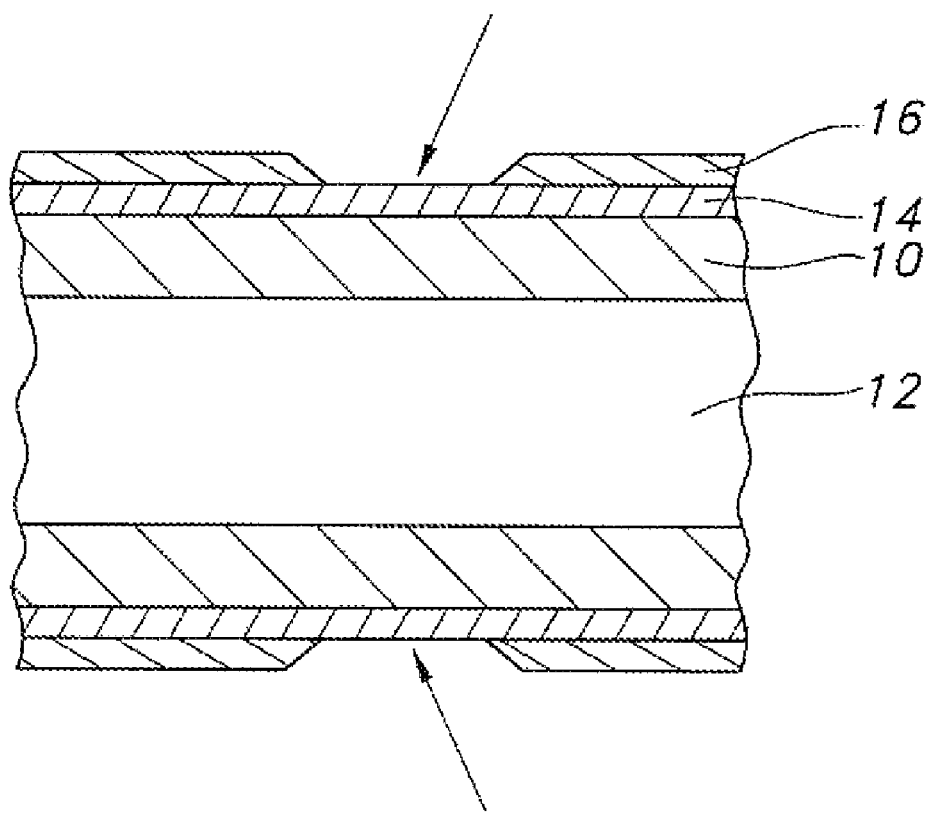
FIG. 2 shows a portion of the coated balloon catheter FIG. 1, showing a portion of a second coating layer abraded.

After applying the second coating layer 16 solution, the solvent may be allowed to evaporate, such as by exposure to ambient conditions for a suitable time period. In one embodiment, the solvent is allowed to evaporate for a period of from 15 to 180 minutes. It is preferable to accomplish this evaporation in such a manner as to minimize the accumulation of water in the uncured coating film resulting from hygroscopic attraction of atmospheric moisture to the polyvinylpyrrolidone. This can be accomplished readily by minimizing the evaporation time, reducing the ambient humidity, elevating the ambient temperature for drying, or using a combination of these methods. As discussed above, the device may be hung from a proximal end, such as a proximal end (not shown) of a balloon catheter as shown in FIG. 1, whereby the second coating layer 16 solution is drawn by gravity towards the distal tip of the device.

The second coating layer 16 is then cured, substantially according to the procedure set forth above for the first coating layer 14. Without being held to any particular theory, it is believed that this step of curing the second coating layer 16, in addition to providing a desirable cross-linking reaction, provides a degree of interpenetration of the polyvinylpyrrolidone-rich second coating layer 16 into the poly(ethylene oxide)-rich first coating layer 14. As discussed above, the cure time and temperature may vary with the choice of isocyanate and polyol and the composition of the substrate 10. For example, the balloon associated with a balloon catheter is typically more fragile than the catheter shaft, and will require a longer curing time at a lower temperature.

Cure temperatures may range from 35° F. to 350° F. although a temperature of from about 180° F. to about 250° F. may be desirable to prevent moisture absorption by the second coating layer 16 during the curing operation. Cure times may vary from 2 minutes to 72 hours or longer, according to the reactivity of the isocyanate and polyol and the selected cure temperature. A caveat is that the cure conditions (time, temperature, etc.) will be maintained to be non-deleterious to the underlying first coating layer 14 and the substrate.

After the second coating layer 16 is cured, it may be rinsed or soaked, for example in water, to remove any uncomplexed polyvinylpyrrolidone which may remain. Generally a brief rinse of 10-15 seconds is sufficient, however a longer rinse or soak is acceptable since the coating is cured and forms a stable gel when in contact with water. After the rinse, the coating may be dried either at ambient temperature or at elevated temperatures.

It will be appreciated that additional reagents may be included in the first and second coating layer mixtures as needed, in accordance with desired reaction conditions to be achieved or desired properties of the finished coating layers. Conventional additives include surfactants, viscosity and flow control agents, antioxidants, pigments, air release agents, and catalysts.

For example, surfactants or wetting agents may be included to promote wetting to the substrate 10 or underlying coating layer, as well as adhesion by the reaction mixture. Examples of useful wetting agents include without limitation: perfluoroalkyl ethoxylate mixtures, 2,4,7,9-tetramethyl 1-5 decyn 4,7-diol and ethylene oxide adducts thereof, 3,5-dimethyl-1,-hexyn 3 ol, condensation products of ethylene oxide and di(isohexyl-isoheptyl) phenol, condensation products of stearylamine and ethylene oxide, nonyl phenoxypoly(ethyleneoxy) ethanol, and polyethoxylated octylphenol.

Viscosity and flow control agents may be used to adjust the viscosity and thixotropy to a desired level. Desirably, the viscosity of the coating mixtures will be such that the coatings can be formed on the substrate at the desired thickness. Viscosities of from 50 cps to 500 cps can be used although higher or lower viscosities may be desirable in certain instances. Viscosity control agents include but are not limited to fumed silica, cellulose acetate butyrate and ethyl acrylate/2-ethyl hexyl acrylate copolymer. Flow control agents, the nature and properties of which are well known to the skilled artisan in this field, may be used in amounts from 0.05 to 5 percent by weight of coating.

Antioxidants may be used to improve oxidative stability of the cured coatings and include without limitation tris(3,5-di-t-butyl-4-hydroxy benzyl) isocyanurate, 2,2'-methylenebis (4 methyl-6-t-butyl phenol), 1,3,5 Trimethyl-2,4,6-tris (3,5-di-t-butyl-4-hydroxybenzyl) benzene, butyl hydroxy toluene, octadecyl 3,5, di-t-butyl 4-hydroxyhydrocinnamate, 4,4'-methylenebis(2,6-di-t-butylphenol), p,p'-dioctyl diphenylamine, 1,1,3-tris-(2-methyl-4-hydroxy-5-t-butylphenyl)

butane. Antioxidants, when included, may be used in amounts from 0.01 to 1 percent by weight of coating.

Conventional pigments can be added to impart color or radiopacity, or to increase the desirable appearance of the coatings. Air release agents (defoamers) include but are not limited to polydimethyl siloxanes, 2,4,7,9-tetramethyl-5-decyn-4 7-diol, 2-ethylhexyl alcohol, n-beta-aminoethyl-gamma-amino-propyl-trimethoxysilane. Air release agents, when included, may be used in amounts from 0.005 to 0.5 percent by weight of coating.

Depending upon the particular isocyanates and polyols or polyamines selected, a catalyst may or may not be used. In all cases polyurethanes or polyureas result. Tertiary amine catalysts are suitable for use herein, such as N,N-dimethylamino-ethanol, N,N-dimethyl cyclo hexylamine Bis-(2-dimethyl aminoethyl) ether, N,N,N',N'N"-pentamethyl-diethylene triamine, N-ethylmorpholine, and 1-(2-hydroxypropyl) imidizole. Examples of metallic catalysts include, but are not limited to stannous octoate, dibutyl tin dilaurate, dibutyl tin mercaptide, calcium carbonate, ferric acetylacetonate, lead octoate, and dibutyl tin diricinoleate. Where catalysts are used, amounts are typically in the range of 0.05% to 0.5% by weight of coating. Normal catalytic amounts as are known in the art are preferred.

Following are presented examples illustrating embodiments of the present invention. These examples are presented to illustrate the presently contemplated best mode of the invention, and are in no way to be considered limiting.

EXAMPLES

Example 1

A polyurethane/PEO primer coating according to the present invention was prepared by combining the following ingredients into a suitable glass mixing vessel: 3.60 g of a toluene diisocyanate adduct of trimethylolpropane, available as Desmodur L 67 MPA/X; 1.34 g of a modified castor oil polyol, available as Polycin 12; 150 g of a 2.5% (w/w) solution of ~300,000 molecular weight poly(ethylene oxide) available from Sigma Aldrich in methylene bromide solvent; and 595 g of methylene bromide. These ingredients were mixed thoroughly to dissolve the components. This yielded a coating solution of approximately 1% (w/w) concentration, with a NCO/OH ratio of 1.3, and a ratio of polyurethane solids to poly(ethylene oxide) of 1.0.

Next, a polyurethane/PVP top coating according to the present invention was prepared by weighing the following ingredients into a suitable glass mixing vessel: 1.10 g of a toluene diisocyanate adduct of trimethylolpropane, available as Desmodur L 67 MPA/X; 2.25 g of a saturated polyester polyol, available as Desmophen 1800; 100 g of a 5% solution of a polyvinylpyrrolidone (dried for 90 minutes at 250° F. prior to placing in solution), available as Kollidon 90F, in methylene bromide; and 377 g of methylene bromide. These ingredients were mixed thoroughly to dissolve the components. This yielded a coating solution of approximately 1.65% (w/w) concentration, with a NCO/OH ratio of 1.3, and a ratio of polyurethane solids to polyvinylpyrrolidone of 0.4.

A catheter containing a inflated PET balloon was first coated in the above mentioned polyurethane/PEO primer coating by immersing the catheter in the coating at a rate of approximately 2 inches/second, followed by withdrawing the catheter at a rate of approximately 0.3 inches/second. The catheter was allowed to dry in ambient conditions for approximately 20 minutes, followed by baking at 165° F. for a period of 4 hours. The catheter was then coated with in the above mentioned polyurethane/PVP top coating, using the same dipping and baking conditions.

The result was a balloon catheter with a surface which became very lubricious when wetted in warm water, and rubbed firmly between the thumb and forefinger to assess the lubricity. 10 cycles of rubbing a portion of the balloon under running warm water resulted in only a very modest perceived decrease in lubricity when compared to an adjacent portion of the balloon which had not been so rubbed.

Example 2

A polyurethane/PEO primer coating according to the present invention was prepared by combining the following ingredients into a suitable glass mixing vessel: 25.6 g of a toluene diisocyanate adduct of trimethylolpropane, available as Desmodur L 67 MPA/X; 42.4 g of a saturated polyester polyol, available as Desmophen 1800; 1200 g of a 5% (w/w) solution of ~200,000 molecular weight poly(ethylene oxide) available as Polyox WSR N80 NF; and 3528 g of methylene bromide. These ingredients were mixed thoroughly to dissolve the components. This yielded a coating solution of approximately 2.5% (w/w) concentration, with a NCO/OH ratio of 1.3, and a ratio of polyurethane solids to poly(ethylene oxide) of 1.0.

Next, a polyurethane/PVP top coating according to the present invention was prepared by weighing the following ingredients into a suitable glass mixing vessel: 1.12 g of a toluene diisocyanate adduct of trimethylolpropane, available as Desmodur L 67 MPA/X; 0.21 g of a modified castor oil polyol, available as Polycin 12; 322 g of methylene bromide; and 5.0 grams of polyvinylpyrrolidone, available as Kollidon 90F. These ingredients were mixed thoroughly to dissolve the components. This yielded a coating solution of approximately 1.7% (w/w) concentration, with a NCO/OH ratio of 2.6, and a ratio of polyurethane solids to polyvinylpyrrolidone of 0.19.

A catheter containing an inflated PET balloon was first coated in the above mentioned polyurethane/PEO primer coating by immersing the catheter in the coating at a rate of approximately 1 inches/second, followed by withdrawing the catheter at a rate of approximately 0.5 inches/second. The catheter was allowed to dry in ambient conditions for approximately 20 minutes, followed by baking at 165° F. for a period of 1 hour. The catheter was then coated with the above mentioned polyurethane/PVP top coating, using the same dipping conditions, followed by a bake cycle of 165° F. for a period of 4 hours.

The result was a balloon catheter with a surface which became very lubricious when wetted in warm water, and tested by rubbing as described in Example 1. Only a modest decrease in lubricity was observed when the surface was challenged with 10 rubbing cycles as described in Example 1.

Example 3

A polyurea/PEO primer coating according to the present invention is prepared by combining the following ingredients into a suitable glass mixing vessel: 17.0 g of a toluene diisocyanate adduct of trimethylolpropane, available as Desmodur L 67 MPA/X; 1.11 g of a difunctional polyetheramine available as Jeffamine EDR148; 200 g of a 5% (w/w) solution of ~200,000 molecular weight poly(ethylene oxide) available as Alkox R400 in methylene bromide solvent; and 507 g of 1,3-dioxolane solvent. These ingredients are mixed thoroughly to dissolve the components. This yields a coating solution of approximately 3.1% (w/w) concentration, with a NCO/NH ratio of 1.1, and a ratio of polyurea solids to poly (ethylene oxide) of 1.25.

Next, a polyurethane/PVP top coating of the present invention is prepared by weighing the following ingredients into a suitable glass mixing vessel: 5.99 g of a toluene diisocyanate adduct of trimethyloipropane, available as Desmodur L 67 MPA/X; 2.99 g of a castor oil polyol, available as D B Oil; 200 g of a 5% solution of a polyvinylpyrrolidone (dried for 90 minutes at 250° F. before placing in solution), available as Plasdone 90, in 1,3-dioxolane; and 196 g of 1,3-dioxolane.

These ingredients are mixed thoroughly to dissolve the components. This yields a coating solution of approximately 4.2% (w/w) concentration, with a NCO/OH ratio of 1.3, and a ratio of polyurethane solids to polyvinylpyrrolidone of 0.7.

A catheter containing an inflated PET balloon is first coated with the above mentioned polyurea/PEO primer coating by immersing the catheter in the coating at a rate of approximately 1.5 inches/second, followed by withdrawing the catheter at a rate of approximately 0.5 inches/second. The catheter is allowed to dry in ambient conditions for approximately 30 minutes, followed by baking at 165° F. for a period of 4 hours. The catheter is then coated with the above mentioned polyurethane/PVP top coating, using the same dipping and baking conditions.

Example 4

A polyurethane/PEO primer coating according to the present invention is prepared by combining the following ingredients into a suitable glass mixing vessel: 11.7 g of a castor oil modified polyisocyanate product available as Vorite 63; 8.26 g of a polyether polyol available as Poly THF 650; 400 g of a 2.5% (w/w) solution of ~200,000 molecular weight poly(ethylene oxide) available as Alkox R400 in methylene bromide solvent; and 2080 g of methylene bromide solvent. These ingredients are mixed thoroughly to dissolve the components. This yields a coating solution of approximately 1.2% (w/w) concentration, with a NCO/OH ratio of 1.3, and a ratio of polyurethane solids to poly(ethylene oxide) of 2.0.

Next, a polyurea/PVP top coating of the present invention is prepared by weighing the following ingredients into a suitable glass mixing vessel: 3.1 g of a polyisocyanate, available as Baytec MP-080; 0.9 g of a difunctional polyetheramine available as Jeffamine ED 600; 200 g of a 5% solution of a polyvinylpyrrolidone (dried for 120 minutes at 225° F. before placing in solution), available as Plasdone 90, in acetonitrile; and 85.7 g of acetonitrile. These ingredients are mixed thoroughly to dissolve the components. This yields a coating solution of approximately 4.9% (w/w) concentration, with a NCO/NH ratio of 1.4, and a ratio of polyurethane solids to polyvinylpyrrolidone of 0.4.

A catheter containing an inflated PET balloon is first coated with the above mentioned polyurea/PEO primer coating by immersing the catheter in the coating at a rate of approximately 1.2 inches/second, followed by withdrawing the catheter at a rate of approximately 0.4 inches/second. The catheter is allowed to dry in ambient conditions for approximately 20 minutes, followed by baking at 170° F. for a period of 4 hours.

The catheter is then coated with the above mentioned polyurethane/PVP top coating, using the same dipping and baking conditions.

Example 5

A polyurethane/PEO primer coating according to the present invention is prepared by combining the following ingredients into a suitable glass mixing vessel: 8.7 g of an aromatic polyisocyanate product available as Desmodur IL; 6.4 g of a polyether polyol available as Poly THF 1000; 200 g of a 5% (w/w) solution of ~200,000 molecular weight poly (ethylene oxide) available as Alkox R400 in 1,3-dioxolane solvent; and 896 g of methylene bromide solvent. These ingredients are mixed thoroughly to dissolve the components. This yields a coating solution of approximately 2.25% (w/w) concentration, with a NCO/OH ratio of 1.3, and a ratio of polyurethane solids to poly(ethylene oxide) of 1.5.

Next, a polyurethane/PVP top coating of the present invention is prepared by weighing the following ingredients into a suitable glass mixing vessel: 3.1 g of a polyisocyanate, available as Baytec MP-210; 5.31 g of a modified castor oil polyol, available as Polycin 12; 400 g of a 5% solution of a polyvinylpyrrolidone (dried for 4 hours at 205° F. before placing in solution), available as Plasdone 90, in acetonitrile; and 499 g of 1,3-dioxolane. These ingredients are mixed thoroughly to dissolve the components. This yields a coating solution of approximately 4.5% (w/w) concentration, with a NCO/OH ratio of 1.1, and a ratio of polyurethane solids to polyvinylpyrrolidone of 0.6.

Then, a catheter containing an inflated PET balloon is first coated with the above mentioned polyurea/PEO primer coating by immersing the catheter in the coating at a rate of approximately 1.0 inches/second, followed by withdrawing the catheter at a rate of approximately 0.3 inches/second. The catheter is allowed to dry in ambient conditions for approximately 20 minutes, followed by baking at 175° F. for a period of 3.5 hours.

The catheter is then coated with the above mentioned polyurethane/PVP top coating, using the same dipping and baking conditions.

Example 6

A polyurea/PEO primer coating according to the present invention is prepared by combining the following ingredients into a suitable glass mixing vessel: 26 g of a toluene diisocyanate adduct of trimethylolpropane, available as Desmodur L 67 MPA/X; 4.6 g of a trifunctional polyetheramine available as Jeffamine T-403; 400 g of a 5% (w/w) solution of ~100,000 molecular weight poly(ethylene oxide) available as Alkox 8150 in methylene bromide solvent; and 1329 g of acetonitrile solvent. These ingredients are mixed thoroughly to dissolve the components. This yields a coating solution of approximately 2.5% (w/w) concentration, with a NCO/NH ratio of 1.3, and a ratio of polyurea solids to poly(ethylene oxide) of 1.2.

Next, a polyurea/PVP top coating according to the present invention is prepared by weighing the following ingredients into a suitable glass mixing vessel: 10.0 g of a toluene diisocyanate adduct of trimethylolpropane, available as Desmodur L 67 MPA/X' 3.3 g of a difunctional polyetheramine available as Jeffamine ED 600; 400 g of a 5% solution of a polyvinylpyrrolidone (dried overnight at 180° F. before placing in solution), available as Kollidon 90F, in methylene bromide; and 1405 g of methylene bromide. These ingredients are mixed thoroughly to dissolve the components. This yields a coating solution of approximately 1.65% (w/w) concentration, with a NCO/NH ratio of 1.3, and a ratio of polyurea solids to polyvinylpyrrolidone of 0.5.

A catheter containing an inflated PET balloon is first coated with the above mentioned polyurea/PEO primer coating by immersing the catheter in the coating at a rate of approximately 2.0 inches/second, followed by withdrawing the catheter at a rate of approximately 0.5 inches/second. The catheter is allowed to dry in ambient conditions for approximately 20 minutes, followed by baking at 150° F. for a period of 8 hours.

The catheter is then coated with the above mentioned polyurethane/PVP top coating, using the same dipping and baking conditions.

COMPARATIVE EXAMPLES

Comparative Example 1

For comparison, a balloon catheter as described in Example 1 was coated in the polyurethane/PVP top coating as described in Example 1, but without first coating with the polyurethane/PEO primer coating. The coating was applied by dipping, and dried and baked as described in Example 1.

The result was a balloon catheter with a surface which became very lubricious when wetted in warm water. However, the coating was easily removed by rubbing as described above. After less than 10 cycles of rubbing, the surface of the balloon had become noticeably less lubricious.

Comparative Example 2

For comparison, a polyurethane primer coating was prepared by combining the following ingredients into a suitable glass mixing vessel: 13.8 g of a toluene diisocyanate adduct of trimethylolpropane, available as Desmodur L 67 MPA/X; 6.1 g a modified castor oil polyol, available as Polycin 12; and 364 g of butyl acetate solvent. These ingredients were mixed thoroughly to dissolve the components. This yielded a polyurethane primer solution of approximately 4% (w/w) concentration, with a NCO/NH ratio of 1.1.

A polyurethane/PVP top coating was prepared substantially as described in Example 1 by weighing the following ingredients into a suitable glass mixing vessel: 1.10 g of a toluene diisocyanate adduct of trimethylolpropane, available as Desmodur L 67 MPA/X; 2.25 g of a saturated polyester polyol, available as Desmophen 1800; 100 g of a 5% solution of a polyvinylpyrrolidone (dried for 90 minutes at 250° F. before placing in solution), available as Kollidon 90F, in methylene bromide; and 377 g of methylene bromide. These ingredients were mixed thoroughly to dissolve the components. This yielded a coating solution of approximately 1.65% (w/w) concentration, with a NCO/OH ratio of 1.3, and a ratio of polyurethane solids to polyvinylpyrrolidone of 0.4.

Then, a catheter containing an inflated PET balloon was dipped in the polyurethane primer at a rate of approximately 2 inches/second, followed by withdrawing the catheter at a rate of approximately 0.3 inches/second. The catheter was allowed to dry in ambient conditions for approximately 20 minutes, followed by baking at 165° F. for a period of 4 hours.

The catheter was then coated with in the above mentioned polyurethane/PVP top coating, using the same dipping and baking conditions.

The result was a balloon catheter with a surface which became very lubricious when wetted in warm water, and rubbed firmly between the thumb and forefinger to assess the lubricity. However, after rubbing the surface 10 times, a noticeable loss of lubricity was observed, compared to a balloon catheter coated using a polyurethane/PEO primer as described in Example 1. This demonstrated that even with a polyurethane primer which adhered to the balloon, the lubricious topcoat was less durable compared to a primer coat comprising polyurethane/PEO or polyurea/PEO composition.

The skilled artisan will appreciate that after formation of the coating in accordance with the disclosure as set forth herein, the coating can imbibe water from an aqueous solution prior to introduction to the body and can become lubricious. Alternatively, the coating can imbibe water solely from body fluids, even if not introduced to water prior to introduction into the body. Because the coating is a cross-linked system, it adheres well to the substrate and/or underlying coating even when hydrated. It can be dried and remoistened repeatedly and it will retain its lubricating properties.

Even further, the two-layer coating as described herein provides further advantages over conventional hydrophilic coatings for substrates such as medical devices. The first, poly(ethylene oxide)-based coating 14 resists abrasion, and exhibits superior durability. The second, polyvinylpyrrolidone-based coating 16 provides a hydrophilic, layer which is more lubricious, but less durable than the first coating. In the event that a portion of the second coating layer becomes worn or abraded (see arrows in FIG. 2), the first, more durable coating layer 14 remains and provides a lubricious surface. Even further, it is believed that even in the event of wear or abrasion of the second coating layer 16, a polyvinylpyrrolidone-rich portion remains in the abraded area due to interpenetration of the second coating layer 16 with the first coating layer 14, improving lubriciousness of the coating as a whole over that found in a conventional poly(ethylene oxide)- or polyvinylpyrrolidone-based coating.

Thus, even in the event of wear or abrasion, a medical device or other substrate 10 coated with a two-layer coating according to the present disclosure shows improved properties of hydrophilicity/lubriciousness compared to conventional poly(ethylene oxide)- or polyvinylpyrrolidone-based coatings. The present coating can be dried and remoistened repeatedly while retaining its lubricating properties.

Finally, one of ordinary skill in the art will recognize that additional embodiments are also possible without departing from the teachings of the present invention. This detailed description, and particularly the specific details of the exemplary embodiments disclosed herein, is given primarily for clarity of understanding, and no unnecessary limitations are to be implied, for modifications will become obvious to those skilled in the art upon reading this disclosure and may be made without departing from the spirit or scope of the invention. Relatively apparent modifications, of course, include combining the various features of one or more figures with the features of one or more of other figures.

The invention claimed is:

1. A hydrophilic, lubricious coating for a substrate, comprising:
   a first hydrophilic, lubricious coating layer selected from the group consisting of a cross-linked polyurethane and a poly(ethylene oxide) or a cross-linked polyurea and a poly(ethylene oxide), wherein the polyurethane is formed by reacting an isocyanate and a polyol and the polyurea is formed by reacting an isocyanate and a polyamine; and
   a second hydrophilic, lubricious coating layer selected from the group consisting of a cross-linked polyurethane and a polyvinylpyrrolidone or a cross-linked polyurea and a polyvinylpyrrolidone, wherein the polyurethane is formed by reacting an isocyanate and a polyol and the polyurea is formed by reacting an isocyanate and a polyamine;
   wherein the first coating layer is covered by the second coating layer and the second coating layer interpenetrates the first coating layer.

2. The coating of claim 1, wherein the poly(ethylene oxide) has an average molecular weight of from about 100,000 to about 600,000.

3. The coating of claim 1, wherein the polyvinylpyrrolidone has an average molecular weight of from about 50,000 to about 2.5 million.

4. The coating of claim 1, wherein the stoichimetric ratio of total isocyanate NCO groups to total polyol OH groups or to total polyamine NH groups in the first coating layer is from about 1.05:1 to about 1.3:1.

5. The coating of claim 4, wherein the stoichimetric ratio of total isocyanate NCO groups to total polyol OH groups or to total polyamine NH groups in the first coating layer is about 1.1:1

6. The coating of claim 1, wherein the stoichimetric ratio of total isocyanate NCO groups to total polyol OH groups or to total polyamine NH groups in the second coating layer varies from about 1.05:1 to about 1.5:1.

7. The coating of claim 6, wherein the stoichimetric ratio of total isocyanate NCO groups to total polyol OH groups or to total polyamine NH groups in the second coating layer is about 1.3:1.

8. A method for providing a hydrophilic, lubricious coating on an exterior surface of a substrate, comprising:
    applying a first coating layer comprising a mixture of an isocyanate, one of polyol or a polyamine, and a poly(ethylene oxide);
    curing the first coating layer to provide a first hydrophilic, lubricious coating comprising one of a cross-linked polyurethane or a cross-linked polyurea and a poly(ethylene oxide);
    applying a second coating layer comprising a mixture of an isocyanate, one of a polyol or a polyamine, and a polyvinylpyrrolidone; and
    curing the second coating layer to provide a second hydrophilic, lubricious coating comprising one of a cross-linked polyurethane or a cross-linked polyurea and a polyvinylpyrrolidone;
    wherein the first coating layer is covered by the second coating layer and the second coating layer interpenetrates the first coating layer.

9. The method of claim 8, wherein the mixture of isocyanate, polyol or polyamine, and poly(ethylene oxide) is dissolved in a solvent selected from the group consisting of methylene bromide, methylene chloride, chloroform, dichloroethane, dichloroethylene, acetonitrile, dibromoethane, methyl benzoate, benzyl acetate, n-propyl bromide, cyclohexanone, 1,3-dioxolane, N-methyl pyrrolidone, and mixtures thereof.

10. The method of claim 8, wherein the mixture of isocyanate, polyol or polyamine, and polyvinylpyrrolidone is dissolved in a solvent selected from the group consisting of methylene bromide, methylene chloride, chloroform, dichloroethane, dichloroethylene, acetonitrile, dibromoethane, n-propyl bromide, 1,3-dioxolane, N-methyl pyrrolidone and mixtures thereof.

11. The method of claim 8, wherein the first coating layer and the second coating layer are applied by any one of dipping, spraying, brushing, rolling, or wiping.

12. The method of claim 8, wherein the step of curing the first coating layer or the second coating layer is accomplished by baking at a temperature of from about 75° F. to about 350° F. for a time period of from about 2 minutes to about 72 hours.

13. The method of claim 8, which includes the step of evaporating the solvent from the first coating layer and the step of evaporating the solvent from the second coating layer prior to the steps of curing.

14. A medical device, comprising:
    a substrate defining a balloon catheter shaft, a balloon, or both;
    a first hydrophilic, lubricious coating layer disposed on the substrate, wherein the first hydrophilic, lubricious coating layer is selected from the group consisting of a cross-linked polyurethane and a poly(ethylene oxide) or a cross-linked polyurea and a poly(ethylene oxide), wherein the polyurethane is formed by reacting an isocyanate and a polyol and the polyurea is formed by reacting an isocyanate and a polyamine; and
    a second hydrophilic, lubricious coating layer which covers the first coating layer, wherein the second hydrophilic, lubricious coating layer is selected from the group consisting of a cross-linked polyurethane and a polyvinylpyrrolidone or a cross-linked polyurea and a polyvinylpyrrolidone, wherein the polyurethane is formed by reacting an isocyanate and a polyol and the polyurea is formed by reacting an isocyanate and a polyamine;
    wherein the second coating layer interpenetrates the first coating layer.

15. The device of claim 14, wherein the polyethylene oxide) has an average molecular weight of from about 100,000 to about 600 000.

16. The device of claim 14, wherein the polyvinylpyrrolidone has an average molecular weight of from about 50,000 to about 2.5 million.

17. The device of claim 14, wherein the stoichimetric ratio of total isocyanate NCO groups to total polyol OH groups or to total polyamine NH groups in the first coating layer mixture is about 1.1:1.

18. The device of claim 14, wherein the stoichimetric ratio of total isocyanate NCO groups to total polyol OH groups or to total polyamine NH groups in the second coating layer mixture is about 1.3:1.

19. The device of claim 14, wherein the medical device is selected from the group consisting of a catheter, a balloon catheter, a urinary catheter, a catheter introducer, a medical wire, a stem, a stent graft, or a dilation balloon.

* * * * *